(12) United States Patent
Sadow et al.

(10) Patent No.: US 10,844,031 B2
(45) Date of Patent: Nov. 24, 2020

(54) GREEN, COPPER-CATALYZED DISPROPORTIONATION OF AROMATIC AND HETEROAROMATIC CARBOXYLATES TO DICARBOXYLATES

(71) Applicant: Iowa State University Research Foundation, Inc., Ames, IA (US)

(72) Inventors: Aaron David Sadow, Ames, IA (US); Zachary Benjamin Weinstein, Ames, IA (US); George A. Kraus, Ames, IA (US)

(73) Assignee: IOWA STATE UNIVERSITY RESEARCH FOUNDATION, INC., Ames, IA (US)

( * ) Notice: Subject to any disclaimer, the term of this patent is extended or adjusted under 35 U.S.C. 154(b) by 0 days.

(21) Appl. No.: 16/685,456

(22) Filed: Nov. 15, 2019

(65) Prior Publication Data
US 2020/0157071 A1    May 21, 2020

Related U.S. Application Data

(60) Provisional application No. 62/768,198, filed on Nov. 16, 2018.

(51) Int. Cl.
*C07D 307/68*    (2006.01)
*C07C 51/15*    (2006.01)

(52) U.S. Cl.
CPC ............ *C07D 307/68* (2013.01); *C07C 51/15* (2013.01)

(58) Field of Classification Search
CPC .............................. C07D 307/68; C07C 51/15
See application file for complete search history.

(56) References Cited

U.S. PATENT DOCUMENTS 2,794,830 A     6/1957  Raecke et al.
9,284,290 B2 *  3/2016  van Haveren ....... C08G 63/181

FOREIGN PATENT DOCUMENTS

DE          936036        12/1955

OTHER PUBLICATIONS

Zhang et al., "Catalytic Synthesis of 2,5-Furandicarboxylic Acid from Furoic Acid: Transformation from C5 Platform to C6 Derivatives in Biomass Utilizations", ACS Sustainable Chem. Eng. 5:9360-9369 (2017).
Weissermel, "Oxidation Products of Xylene and Naphthalene," 4th Ed., Industrial Organic Chemistry, Wiley-VCH GmbH & Co. KGaA, pp. 388-405 (2003).
Ratusky, "Transcarboxylation Reactions of Salts of Organic Acids. XVIII. The Anomalous Course of Transcarboxylation of Salts of Biphenyl Carboxylic Acids," Collect. Czechoslov. Chem. Commun. 37:2436-2450 (1972).
Ratusky, "Transcarboxylation Reactions of Salts of Organic Acids. XV. Salts of Naphthalenecarboxylic Acids as Carboxylating Agents in Transcarboxylation Reactions," Chem. Ind. 42:1347-1349 (1970).
Ratusky, "Transcarboxylation Reactions of Potassium Benzoate and of Potassium Salts of Benzenepolycarboxylic Acids," Collection Czechoslov. Chem. Commun. 32:2504-2511 (1967).
Raecke, "Synthese von Di- und Tricarbonsauren Aromatischer Ringsysteme Durch Verschiebung von Carboxyl-Gruppen" Angew. Chem. 70(1):1-5 (1958).
Banerjee et al., "Carbon Dioxide Utilization via Carbonate-Promoted C-H Carboxylation," Nature 531:215-219 (2016).
Dick et al., "A Scalable Carboxylation Route to Furan-2,5-dicarboxylic Acid," Green Chem. 19:2966-2972 (2017).

(Continued)

*Primary Examiner* — Timothy R Rozof
(74) *Attorney, Agent, or Firm* — Troutman Pepper Hamilton Sanders LLP (Rochester)

(57) ABSTRACT

The present application relates to a process for preparation of a compound of Formula (I) and Formula (IV):

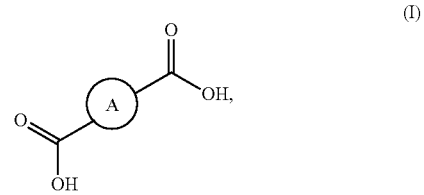

(I)

wherein

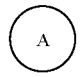

is as described herein; and

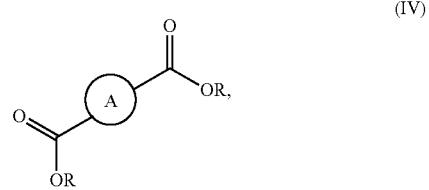
(IV)

wherein

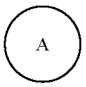

and R are as described herein.

29 Claims, 1 Drawing Sheet

(56) References Cited

OTHER PUBLICATIONS

Pan et al., "Catalytic Conversion of Furfural Into a 2,5-Furandicarboxylic Acid-Based Polyester with Total Carbon Utilization," ChemSusChem 6:47-50 (2013).
Thiyagarajan et al., "Concurrent Formation of Furan-2,5- and Furan-2,4-dicarboxylic Acid: Unexpected Aspects of the Henkel Reaction," RSC Adv. 3:15678-15686 (2013).

* cited by examiner

GREEN, COPPER-CATALYZED DISPROPORTIONATION OF AROMATIC AND HETEROAROMATIC CARBOXYLATES TO DICARBOXYLATES

This application claims the benefit of U.S. Provisional Patent Application Ser. No. 62/768,198, filed Nov. 16, 2018, which is hereby incorporated by reference in its entirety.

This invention was made with government support under CHE1464774 awarded by National Science Foundation. The government has certain rights in the invention.

FIELD

The present application relates to a green, copper-catalyzed disproportionation of aromatic and heteroaromatic carboxylates to dicarboxylates.

BACKGROUND

Sustainable manufacturing of aromatic dicarboxylic acids, such as terephthalic acid (TPA) or 2,5-furandicarboxylic acid (2,5-FDCA) used in polyesters, would benefit from non-oxidative syntheses because their bio-renewable precursors are already partially oxidized. These dicarboxylic acid products are intermediates in large scale, or potentially large scale, polymer synthesis. Terephthalic acid (30 million tons per year as of 2006) is primarily used to manufacture poly(ethylene) terephthalate (PET) for applications in textiles and as food and beverage containers (Sheehan, "Terephthalic Acid, Dimethyl Terephthalate, and Isophthalic Acid," in *Ullmann's Encyclopedia of Industrial Chemistry*, Wiley-VCH Verlag GmbH & Co. KGaA (2011)). Poly (ethylene) furoate (PEF), in which 2,5-FDCA replaces TPA as the dicarboxylate monomer, is an emerging alternative material to PET in part because the oxygen permeability is reduced in the furan-based material compared to PET. The dicarboxylic acids monomers are currently synthesized via harsh catalytic oxidation processes from reduced petrochemical starting materials, for which alternative conditions have been sought (Zuo et al., "Liquid-Phase Oxidation of Toluene and p-Toluic Acid Under Mild Conditions: Synergistic Effects of Cobalt, Zirconium, Ketones, and Carbon Dioxide," *Ind. Eng. Chem. Res.* 47:546-52 (2008); Hamley et al., "Selective Partial Oxidation in Supercritical Water: the Continuous Generation of Terephthalic Acid From Para-Xylene in High Yield," *Green Chem.* 4:235-38 (2002); Dunn et al., "High-Temperature Liquid Water: A Viable Medium for Terephthalic Acid Synthesis," *Environ. Sci. Technol.* 39:5427-35 (2005)). For example, the multistep Amoco process utilizes p-xylene as a precursor to terephthalic acid (Sheehan, "Terephthalic Acid, Dimethyl Terephthalate, and Isophthalic Acid," in *Ullmann's Encyclopedia of Industrial Chemistry*, Wiley-VCH Verlag GmbH & Co. KGaA (2011)) (FIG. 1A). A related oxidation of bio-renewable 5-hydroxymethyl furfural (HMF) is proposed for the commercial manufacture of 2,5-FDCA (FIG. 1B) and further enhances the appeal of PEF in the context of sustainability (Bozell et al., "Technology Development for the Production of Biobased Products From Biorefinery Carbohydrates—the US Department of Energy's "Top 10" revisited," *Green Chem.* 12:539-54 (2010)), but the short shelf life of HMF may generate challenges for this conversion approach (van Putten et al., "Hydroxymethylfurfural, A Versatile Platform Chemical Made From Renewable Resources," *Chem. Rev.* 113:1499-597 (2013)).

The isomerization of isophthalate to terephthalate, known as the Henkel process, was a commercial process prior to the development of the oxidative Amoco process (Raecke, "Synthese von Di-und Tricarbonsäuren aromatischer Ringsysteme durch Verschiebung von Carboxyl-Gruppen," *Angewandte Chemie* 70:1-5 (1958); Arpe et al., *Industrial Organic Chemistry*; 5th ed. Wiley-VCH Weinheim, Germany (2010); U.S. Pat. No. 2,794,830 to Raecke et al.). The challenges facing the Henkel process and related disproportionation or isomerization of aromatic and heteroaromatic carboxylates include high reaction temperatures, highly toxic cadmium-based catalysts (Ratusky et al., "Transcarboxylation Reactions of Salts of Benzene Carboxylic Acids," *Chem. Ind.* 1798-800 (1966)), formation of multiple carboxylate side products (Ratusky, "Transcarboxylation Reactions of Potassium Benzoate and of Potassium Salts of Benzenepolycarboxylic Acids," *Collect. Czech. Chem. Commun.* 32:2504-11 (1967)), and variable dependence on carbon dioxide pressure (Ratusky et al., "Transcarboxylation Reactions of Salts of Benzene Carboxylic Acids," *Chem. Ind.* 1798-800 (1966)).

The state-of-the-art conditions for disproportionation of potassium benzoate involve heating solid mixtures of cadmium(II) iodide and potassium benzoate at 300-450° C. under 10-50 bar of $CO_2$ (Arpe et al., *Industrial Organic Chemistry*; 5th ed. Wiley-VCH Weinheim, Germany (2010); U.S. Pat. No. 2,794,830 to Raecke et al). The isomerization of potassium isophthalate also involves heating mixtures of cadmium(II) iodide and dipotassium isophthalate. Generally, the isomerization reaction occurs at milder temperatures and requires shorter times than disproportionation reaction (Ratusky, "Transcarboxylation Reactions of Salts Organic Acids. XVI. Transcarboxylation of the Salts of Heterocyclic Carboxylic Acids," *Collect. Czech. Chem. Commun.* 36:2831-45 (1971)). The importance of carbon dioxide in both the disproportionation and isomerization reactions that produce terephthalate appears to be sensitive to the other reaction conditions, and reported carbon dioxide pressures vary widely. Initial reports indicate that the higher pressures of $CO_2$ are necessary for conversion (U.S. Pat. No. 2,794,830 to Raecke et al.), but other studies use carbon dioxide generated from carbonate salts (Ogata et al., "The Preparation of Terephthalic Acid From Phthalic or Benzoic Acid,". *J. Am. Chem. Soc.* 79:6005-8 (1957)) or even flowing $N_2$ (Thiyagarajan et al., "Concurrent Formation of Furan-2,5- and Furan-2,4-dicarboxylic Acid: Unexpected Aspects of the Henkel Reaction," *RSC Adv.* 3:15678-86 (2013)).

Catalytic oxidation reactions, used to synthesize 2,5-FDCA from HMF, suffer from the same drawbacks aspxylene oxidation or employ pressure metal catalysts (Verdeguer et al., "Oxydation Catalytique du HMF en Acide 2,5-Furane Dicarboxylique," *J. Mol. Catal.* 85:327-44 (1993); Davis et al., "Oxidation of 5-Hydroxymethylfurfural Over Supported Pt, Pd and Au Catalysts," *Catal. Today* 160:55-60 (2011); Partenheimer et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal=Bromide Catalysts," *Adv. Synth. Catal.* 343:102-11 (2001)). As an alternative to oxidations, Henkel-type disproportionation reactions of furan 2-carboxylate salts may provide 2,5-FDCA. Cadmium iodide catalyzes the redistribution at elevated temperatures (380° C.) under a carbon dioxide atmosphere, similar to the disproportionation of potassium benzoate (Ratusky, "Tran-scarboxylation Reactions of Salts Organic Acids. XVI. Transcarboxylation of the Salts of Heterocyclic Carboxylic Acids," *Collect. Czech. Chem. Commun.* 36:2831-45 (1971); Thiyagarajan et al., "Concurrent Formation of Furan-2,5- and Furan-2,4-dicarboxylic Acid: Unexpected Aspects of the Henkel Reaction," *RSC Adv.* 3:15678-86 (2013)). The formation of both 2,5-FDCA and its 2,4-FDCA isomer (40-59% yield) after 20 min complicate these conversions. Lower temperature (260° C.) and longer reaction time (5.5 hours) affords 2,5-FDCA in improved yield (62%) and selectivity (70%) over 2,4-FDCA. In this case, the reaction was performed under flowing $N_2$ (Thiyagarajan et al., "Concurrent Formation of Furan-2,5- and Furan-2,4-dicarboxylic Acid: Unexpected Aspects of the Henkel Reaction," *RSC Adv.* 3:15678-86 (2013)).

The disproportionation of potassium furancarboxylate to give 2,5-FDCA requires lower temperatures than the corresponding reaction to give TPA. A careful study of the effect of temperature on potassium furoate conversion, total FDCA yield, and selectivity for 2,5-FDCA in a $ZnCl_2$-catalyzed process reveals expectedly that at high conversion with high reaction temperature, product yield decreases from diminished selectivity (Pan et al., "Catalytic Conversion of Furfural into a 2,5-Furandicarboxylic Acid-Based Polyester with Total Carbon Utilization," *Chem Sus Chem* 6:47-50 (2013)). Specifically, the yield of 2,5-FDCA increases from 8% in reactions at 220° C. to 52% at 250° C., but at even higher temperatures and higher conversions, yield decreases (e.g., 13% at 280° C.) as a result of poor selectivity. Recently, a novel non-catalytic approach to synthesizing 2,5-FDCA have been developed from 2-furoic acid and 1.55 equivalents of $Cs_2CO_3$ at low temperatures (200° C.) and moderate pressure (8 bar) in good yield (89%) (Dick et al., "A Scalable Carboxylation Route to Furan-2,5-dicarboxylic Acid," *Green Chem.* 19:2966-72 (2017); Banerjee et al., "Carbon Dioxide Utilization via Carbonate-Promoted C—H Carboxylation," *Nature* 531:215-9 (2016)). This $Cs_2CO_3$-mediated pathway provides 2,5-FDCA exclusively, but reactions of benzoic acid and cesium carbonate provide mixtures of diphthalates, triphthalates, and tetraphthalates.

Several catalysts have been studied in the literature for synthesis of 2,5-FDCA via catalytic disproportionation. When comparing their reported effectiveness toward the disproportionation of potassium furoate, the activity trends $CdI_2 > ZnI_2 > ZnCl_2 > CdCl_2$ (Table 1) (Thiyagarajan et al., "Concurrent Formation of Furan-2,5- and Furan-2,4-dicarboxylic Acid: Unexpected Aspects of the Henkel Reaction," *RSC Adv.* 3:15678-86 (2013); Pan et al., "Catalytic Conversion of Furfural into a 2,5-Furandicarboxylic Acid-Based Polyester with Total Carbon Utilization," *Chem Sus Chem* 6:47-50 (2013)). Iodide salts of Cd and Zn are more effective catalysts for benzoate disproportionation and isophthalate isomerization than other the halides or carbonate counterions (Ogata et al., "The Preparation of Terephthalic Acid From Phthalic or Benzoic Acid,". *J. Am. Chem. Soc.* 79:6005-8 (1957); Revankar et al., "A Kinetic Study of the Disproportionation of Potassium Benzoate," *Ind. Eng. Chem. Res.* 26:1691-95 (1987); Revankar et al., "Kinetics of the Thermal Conversion of Potassium Salts of Benzenedicarboxylic and -Tricarboxylic Acids to Terephthalic Acid," *Ind. Eng. Chem. Res.* 31:781-86 (1992)). $CuCl_2$ salt was not effective for the synthesis of 2,5-FDCA under the same conditions as $Cd_2$ (Thiyagarajan et al., "Concurrent Formation of Furan-2,5- and Furan-2,4-dicarboxylic Acid: Unexpected Aspects of the Henkel Reaction," *RSC Adv.* 3:15678-86 (2013)).

TABLE 1

Literature Evaluation of $MX_2$ Catalyzed Furan Disproportionation

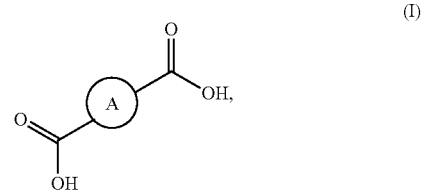

| | $CdCl_2 <$ | $ZnCl_2 <$ | $ZnI_2 <$ | $CdI_2$ |
|---|---|---|---|---|
| Yield (%) | 0 | 31 | 40 | 64 |
| Temp (° C.) | 280 | 260 | 260 | 260 |
| Time (h) | 0.5 | 5.5 | 5.5 | 5.5 |

The present application is directed to overcoming these and other deficiencies in the art.

SUMMARY

One aspect of the present application relates to a process for preparation of a compound of Formula (I):

(I)

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl; or a salt thereof. This process includes:

providing a compound of Formula (II):

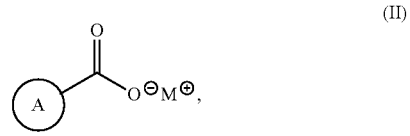

(II)

wherein M is a metal;

providing an oxide of carbon;

providing a copper(I) containing compound; and reacting the compound of Formula (II) with the oxide of carbon in the presence of the copper(I) containing compound to form the compound of Formula (I).

Another aspect of the present application relates to a process for preparation of a compound of Formula (I):

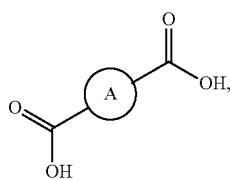

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;

or a salt thereof. This process includes:

providing a compound of Formula (III):

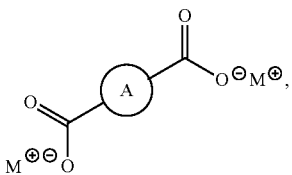

wherein M is a metal;

providing a copper(I) containing compound; and reacting the compound of Formula (III) in the presence of the copper(I) containing compound to form the compound of Formula (I).

Yet another aspect of the present application relates to a process for preparation of a compound of Formula (IV):

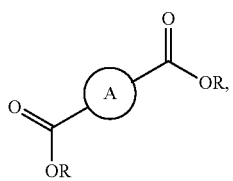

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;

R is $C_{1-6}$ alkyl;

or a salt thereof. This process includes:

providing a compound of Formula (I):

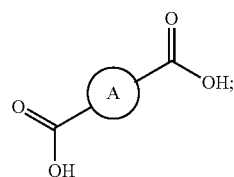

providing an alkylating agent;

reacting the compound of Formula (I) with the alkylating agent to form the compound of Formula (IV).

Another aspect of the present application relates to a process for preparation of a compound of Formula (IV):

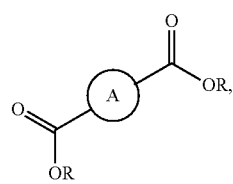

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;

R is $C_{1-6}$ alkyl;

or a salt thereof. This process includes:

providing a compound of Formula (II):

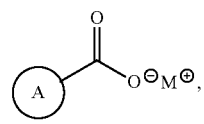

wherein M is a metal;

providing an oxide of carbon;

providing a copper(I) containing compound;

providing an alkylating agent; and reacting the compound of Formula (II) with the oxide of carbon in the presence of the copper(I) containing compound and the alkylating agent to form the compound of Formula (IV).

In order to access dicarboxylic acids from biorenewable sources and provide a better route to 2,5-FDCA towards sustainable PEF, cadmium-free, highly selective catalytic conditions for disproportionation or isomerization of aromatic carboxylates was discovered. CuI-mediated disproportionation of potassium furoate to 2,5-FDCA was studied to advance this approach.

Copper(I) iodide catalyzed the disproportionation of aromatic and heteroaromatic carboxylic acids to give dicarboxylic acids. Potassium furoate heated to 280-300° C. in the presence of 10 mol % CuI under carbon dioxide (40 bar) formed dipotassium 2,5-furandicarboxylate (2,5-FDCK), which was isolated as pure 2,5-dicarboxylic acid (2,5-FDCA) in up to 75% isolated yield. The crude product formed with excellent selectivity for the 2,5-furandicarboxylate over the regioisomeric 2,4-furandicarboxylate (92% selectivity). Starting materials were recovered in experiments lacking CuI or with pressurized $N_2$ replacing $CO_2$, whereas high conversion and low yields of 2,5-FDCA were obtained with moderate $CO_2$ pressures, suggesting several roles for carbon dioxide in the transformation. Similarly, potassium benzoate heated to 320-350° C. the presence of 10 mol % CuI under carbon dioxide (40 bar) produced terephthalic acid after workup in up to 60% yield.

BRIEF DESCRIPTION OF THE DRAWINGS

FIG. 1A shows the synthesis of terephthalic acid. FIG. 1B shows the synthesis of 2,5-furandicarboxylic acid.

DETAILED DESCRIPTION

Figures 1A, 1B:
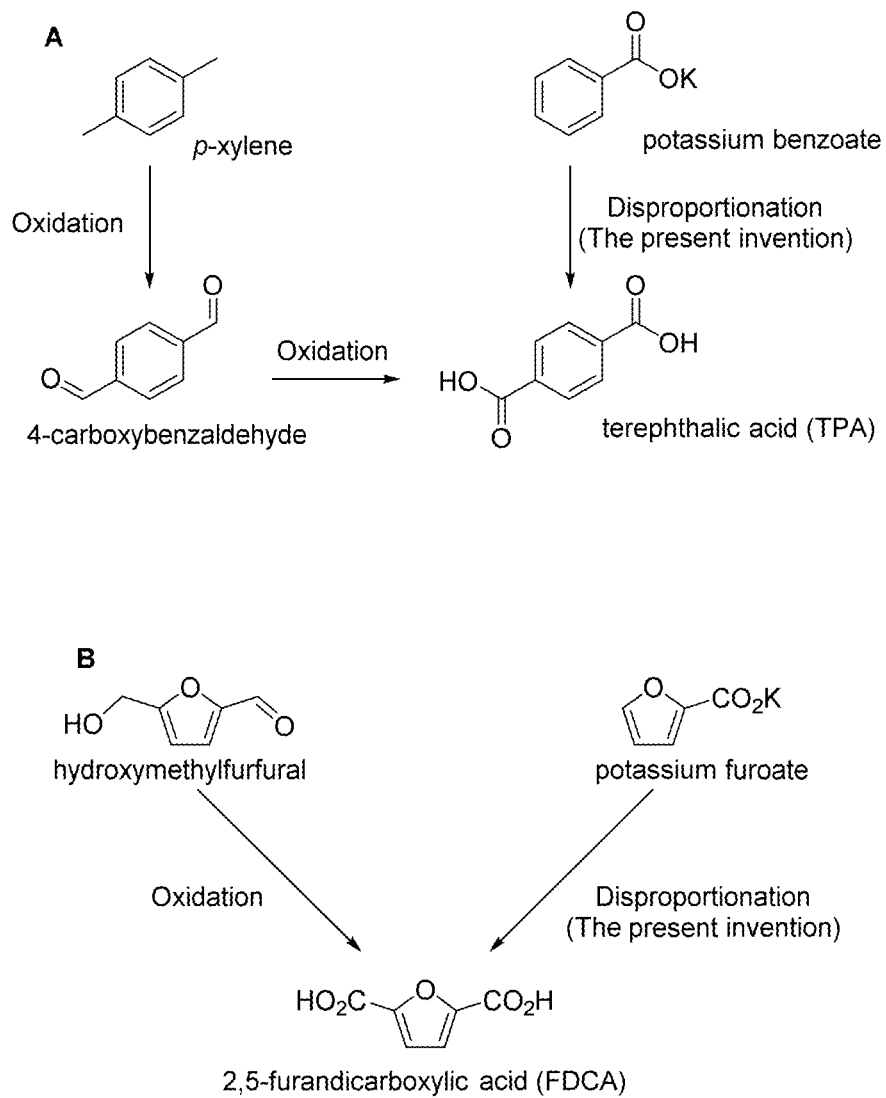
FIGS. 1A-B show alternative ways to prepare dicarboxylates. Dicarboxylates are often prepared through oxidation. Disproportionation reactions provide an alternative route towards synthesizing diacids.

One aspect of the present application relates to a process for preparation of a compound of Formula (I):

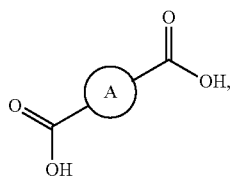

(I)

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl; or a salt thereof. This process includes:
  providing a compound of Formula (II):

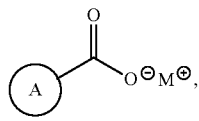

(II)

wherein M is a metal;
  providing an oxide of carbon;
  providing a copper(I) containing compound; and
  reacting the compound of Formula (II) with the oxide of carbon in the presence of the copper(I) containing compound to form the compound of Formula (I).

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkali metal" or "alkali metal atom" refers to metals listed in Group 1 (IA) of the Periodic Table of Elements. Alkali metals include lithium (Li), sodium (Na), potassium (K), rubidium (Rb), cesium (Cs), and francium (Fr).

The term "alkyl" refers to an aliphatic hydrocarbon group which may be straight or branched having about 1 to about 15 carbon atoms in the chain. Branched means that one or more lower alkyl groups such as methyl, ethyl, or propyl are attached to a linear alkyl chain. Exemplary alkyl groups include methyl, ethyl, n-propyl, i-propyl, n-butyl, t-butyl, n-pentyl, and 3-pentyl.

The term "cycloalkyl" refers to a non-aromatic, saturated or unsaturated, mono- or multi-cyclic ring system of about 3 to about 8 carbon atoms, or of about 5 to about 7 carbon atoms, and which may include at least one double bond. Exemplary cycloalkyl groups include, without limitation, cyclopropyl, cyclobutyl, cyclopentyl, cyclohexyl, cycloheptyl, cyclopropenyl, cyclobutenyl, cyclopentenyl, cyclophenyl, anti-bicyclopropane, and syn-tricyclopropane.

The term "aryl" refers to an aromatic monocyclic or multi-cyclic (polycyclic) ring system of 6 to about 19 carbon atoms, or of 6 to about 10 carbon atoms. The ring system of the aryl group may be optionally substituted. For purposes of this application, the aryl may be a monocyclic, or a polycyclic ring system, which may be fused. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". For purposes of this application, the heteroaryl may be a monocyclic, or a polycyclic ring system, which may be fused. Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxopyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydrobenzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

The term "halogen" means fluoro, chloro, bromo, or iodo.

The term "phenyl" means a phenyl group as shown below:

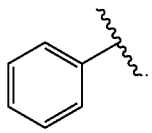

"Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, aryl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

One embodiment relates to compounds of Formula (I) where

is selected from the group consisiting of binaphtyl, biphenyl, phenyl, and furyl, wherein the binaphtyl, biphenyl, phenyl, and furyl can be optionally substituted from 1 to 3 times with a substituent selected independently at each occurrence thereof from $C_{1-6}$ alkyl, $C_{3-8}$ cycloalkyl, aryl, and heteroaryl.

Another embodiment relates to compounds of Formula (I) where

is selected from the group consisting of fused aryl and fused heteroaryl, wherein the fused aryl and fused heteroaryl can be optionally substituted from 1 to 3 times with a substituent selected independently at each occurrence thereof from $C_{1-6}$ alkyl, $C_{3-8}$ cycloalkyl, aryl, and heteroaryl.

In one embodiment, the oxide of carbon is carbon dioxide.

In another embodiment, the copper(I) containing compound is a copper(I) halide. Preferably, the copper(I) containing compound is CuI.

In another embodiment, M is an alkali metal. Preferably, M is K or Na.

The copper(I) containing compound is present in an amount of from 0.001 to 25 mol %. Preferably, from 0.01 to 25 mol %, from 0.01 to 20 mol %, from 0.01 to 15 mol %, from 0.1 to 15 mol %, from 1 to 15 mol %, from 5 to 15 mol %, from 5 to 10 mol %.

Reaction of the compound of Formula (II) with the oxide of carbon in the presence of the copper(I) containing compound can be carried out at a pressure ranging from 1 to 73.8 bar. Preferably, from 5 to 73.8 bar, from 5 to 70 bar, from 10 to 70 bar, from 10 to 65 bar, from 15 to 65 bar, from 15 to 60 bar, from 20 to 60 bar, from 25 to 60 bar, from 25 to 55 bar, from 30 to 55 bar, from 30 to 50 bar, from 30 to 45 bar, from 35 to 45 bar.

Reaction can be carried out at a temperature above 250° C. and below the decomposition temperature of the compound of Formula (II). Preferably, at a temperature above 260° C. and below 400° C., at a temperature above 270° C. and below 400° C., at a temperature above 280° C. and below 400° C., at a temperature above 260° C. and below 390° C., at a temperature above 260° C. and below 380° C., at a temperature above 260° C. and below 370° C., at a temperature above 260° C. and below 360° C., at a temperature above 270° C. and below 360° C., at a temperature above 280° C. and below 360° C., at a temperature above 290° C. and below 360° C., at a temperature above 300° C. and below 360° C., at a temperature above 300° C. and below 350° C., at a temperature above 300° C. and below 340° C.

Reaction can be carried out for a period of time ranging from seconds to several days. Preferably, from 0.0005 to 24 hours, from 0.005 to 24 hours, from 0.05 to 24 hours, from 0.05 to 23 hours, from 0.05 to 22 hours, from 0.05 to 21 hours, from 0.05 to 20 hours, from 0.05 to 19 hours, from 0.05 to 18 hours, from 0.05 to 17 hours, from 0.05 to 16 hours, from 0.05 to 15 hours, from 0.05 to 14 hours, from 0.05 to 13 hours, from 0.05 to 12 hours, from 0.05 to 11 hours, from 0.05 to 10 hours, from 0.05 to 9 hours, from 0.05 to 8 hours, from 0.05 to 7 hours, from 0.05 to 6 hours, from 0.05 to 5 hours, from 0.1 to 5 hours, from 0.2 to 5 hours, from 0.3 to 5 hours, from 0.4 to 5 hours, from 0.5 to 5 hours.

In one embodiment, the process further includes mixing the compound of Formula (II) with the copper(I) containing compound prior to said reacting.

Mixing is conducted for several minutes. Preferably, mixing is conducted for at least 1 minute, for at least 2 minutes, for at least 3 minutes, for at least 4 minutes, for at least 5 minutes, for at least 6 minutes, for at least 7 minutes, for at least 8 minutes, for at least 9 minutes, for at least 10 minutes.

In another embodiment, the process further includes:
providing an alkylating agent; and
reacting the compound of Formula (I) with the alkylating agent to form the compound of Formula (IV):

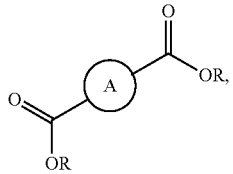

wherein R is $C_{1-6}$ alkyl.

Suitable alkylating agent is R—W, where W is OH, halogen, —$OSO_2CF_3$, $OSO_2C_6H_4Me$, or an alkene in the presence of p-toluenesulfonic acid.

In another embodiment, the reacting leads to formation of a reaction mixture. This process further includes dissolving the reaction mixture in the hot water.

In yet another embodiment, the process further includes filtering the dissolved reaction mixture.

In a further embodiment, the process further includes acidifying the filtered reaction mixture using a mineral acid.

Another aspect of the present application relates to a process for preparation of a compound of Formula (I):

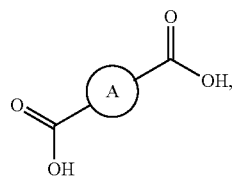

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;
or a salt thereof. This process includes:
providing a compound of Formula (III):

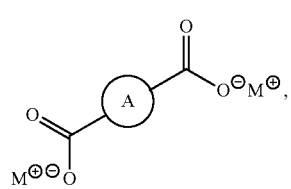

wherein M is a metal;
providing a copper(I) containing compound; and
reacting the compound of Formula (III) in the presence of the copper(I) containing compound to form the compound of Formula (I).

Yet another aspect of the present application relates to a process for preparation of a compound of Formula (IV):

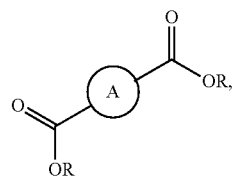

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;
R is $C_{1-6}$ alkyl;
or a salt thereof. This process includes:
providing a compound of Formula (I):

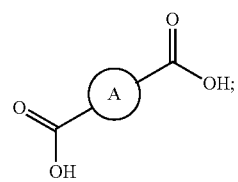

providing an alkylating agent;
reacting the compound of Formula (I) with the alkylating agent to form the compound of Formula (IV).

One embodiment relates to compounds of Formula (IV) where

is selected from the group consisting of binaphtyl, biphenyl, phenyl, and furyl, wherein the binaphtyl, biphenyl, phenyl, and furyl can be optionally substituted from 1 to 3 times with a substituent selected independently at each occurrence thereof from $C_{1-6}$ alkyl, $C_{3-8}$ cycloalkyl, aryl, and heteroaryl.

Another embodiment relates to compounds of Formula (IV) where

is selected from the group consisting of fused aryl and fused heteroaryl, wherein the fused aryl and fused heteroaryl can be optionally substituted from 1 to 3 times with a substituent selected independently at each occurrence thereof from $C_{1-6}$ alkyl, $C_{3-8}$ cycloalkyl, aryl, and heteroaryl.

Another aspect of the present application relates to a process for preparation of a compound of Formula (IV):

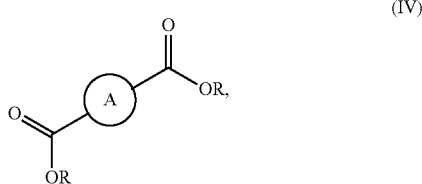

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;

R is $C_{1-6}$ alkyl;

or a salt thereof. This process includes:
providing a compound of Formula (II):

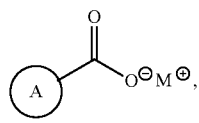

wherein M is a metal;
providing an oxide of carbon;
providing a copper(I) containing compound;
providing an alkylating agent; and
reacting the compound of Formula (II) with the oxide of carbon in the presence of the copper(I) containing compound and the alkylating agent to form the compound of Formula (IV).

The present application may be further illustrated by reference to the following examples.

EXAMPLES

Example 1—Materials and Methods

All reactions were performed in a Parr autoclave reactor. Copper (I) iodide (Alfa) was used as received. Furoic acid, benzoic acid, and isophthalic acid were obtained from Sigma-Aldrich and used as received for the synthesis of carboxylate substrates. Potassium carboxylates were synthesized by reactions of respective acids and potassium hydroxide in ethanol, resulting in precipitation of the carboxylate from the ethanol solution. The product was washed with ethanol and dried under vacuum at 100° C. $^1H$ and $^{13}C\{^1H\}$ NMR spectra were recorded with a Bruker Avance III 600 or Varian MR-400 spectrometer. Infrared spectra were measured on a Bruker Vertex 80 FTIR spectrometer, and diffuse reflectance experiments were performed using a Harrick Praying Mantis apparatus. XPS measurements were performed using a Kratos Amicus/ESCA 3400 instrument (240 W unmonochromated MgKa radiation) and photoelectrons emitted at 00 from the surface normal were energy analyzed using a DuPont type analyzer.

Example 2—Synthesis of 2,5-Furan Dicarboxylic Acid From Potassium Furoate

Dried potassium furoate (262 mg, 1.75 mmol) and copper (I) iodide (33 mg, 0.17 mmol) were mixed in mortar and pestle, and then transferred to a test tube. The test tube was placed in an aluminum block inside a Parr reactor. The reactor was charged and vented with $CO_2$ three times to remove the ambient atmosphere. The reactor was pressurized with $CO_2$ (40 bar) and then heated at the desired temperature for a set time (e.g., 300° C. for 16 hours). The vessel was allowed to cool to room temperature, and then the pressure was released. The crude product was typically a reddish-black solid, which was dissolved in hot water. The solution was filtered through charcoal and a glass frit and then acidified with HCl (aq) to precipitate a white solid. The suspension was allowed to stand for 1 hour, the mixture was centrifuged, the supernatant was decanted, and the solid washed with water. The white solid was dried, yielding pure 2,5-FDCA (73.5 mg, 0.47 mmol, 54%). The supernatant and wash solutions were combined. After extraction with DMSO, it was determined that the wash solutions contained KCl (118.3 mg, 1.59 mmol), furoic acid (5.6 mg, 0.05 mmol), 2,4-FDCA (8.3 mg, 0.05 mmol), and 2,5-FDCA (31.0 mg, 0.20 mmol). The combined 2,5-FDCA from soluble and insoluble portions gave 78.5% total yield, and 90.8% of KCl was recovered from the aqueous phase.

Example 3—Synthesis of 2,5-Furan Dicarboxylic Acid From Sodium Furoate

Dried sodium furoate (235 mg, 1.75 mmol) and copper (I) iodide (33 mg, 0.17 mmol) were thoroughly mixed in a mortar and pestle and then transferred to a glass test tube. The test tube was placed in an aluminum block inside of a Parr reactor. The reactor was charged and vented with $CO_2$ three times to remove air. The reactor was pressurized with $CO_2$ (40 bar), heated to 340° C. for 2 hours, and then allowed to cool to room temperature. The reactor was vented slowly. The crude product was obtained as a reddish-black solid, which was dissolved in hot water. The solution was filtered through charcoal and a glass frit, and then the solution was acidified with HCl (aq) to precipitate a white solid. The mixture was allowed to stand for 1 hour, and then it was centrifuged, the supernatant was decanted, and the solid washed with water. The white solid was dried, yielding pure 2,5-FDCA (80 mg, 0.51 mmol, 58.3% yield).

Example 4—Synthesis of Terephthalic Acid From Potassium Benzoate

Dried potassium benzoate (108 mg, 0.67 mmol) was ground together with copper (I) iodide (13 mg, 0.07 mmol) into a clean test tube. The test tube was placed in an aluminum block inside of a Parr reactor. The reactor was charged and vented with $CO_2$ three times to remove air. After degassing for the final time, the reactor was charged with $CO_2$ (40 bar). The reactor was placed in a heating mantle and heated to 350° C. for 2 hours and then cooled to room temperature. The reactor was vented slowly and the reddish-black solid was removed from the test tube, and dissolved in hot water. The solution was filtered through a small charcoal layer over a glass filter plug, and was acidified with HCl (aq) precipitating out a white solid. After standing for one hour, the mixture was centrifuged, the supernatant decanted, and the solid washed with water. The white solid was dried, yielding terephthalic acid (28 mg, 0.17 mmol, 50.7% yield).

Example 5—Synthesis of Terephthalic Acid From Dipotassium Isophthalate

Dried dipotassium isophthalate (188 mg, 0.78 mmol) and copper (I) iodide (15 mg, 0.08 mmol) were mixed in a mortar and pestle and transferred to a test tube. The test tube was placed in an aluminum block inside of a Parr reactor. The reactor was charged and vented with $CO_2$ three times to remove air. After degassing for the final time, the reactor was charged with $CO_2$ (40 bar). The reactor was placed in a heating mantle and heated to 350° C. for 3 hours and then cooled to room temperature. The reactor was vented slowly and the reddish-black solid was removed from the test tube, and dissolved in hot water. The solution was filtered through a small charcoal layer over a glass filter plug, and was acidified with HCl (aq) precipitating out a white solid. After standing for one hour, the mixture was centrifuged, the supernatant decanted, and the solid washed with water. The white solid was dried, yielding a mixture of terephthalic acid and isophthalic acid at a ratio of roughly 1:4 respectively by $^1$H NMR spectroscopy (90 mg, 0.54 mmol, 69% recovery).

Example 6—Results and Discussion of Examples 1-5

The Henkel reaction occurs at high temperatures at a solid-solid interface of an inhomogeneous mixture of substrate and catalyst. To mitigate heat transfer issues and temperature gradients that might influence reproducibility, an aluminum insert for a stainless-steel Parr autoclave reactor with evenly distributed slots for four glass reaction vessels and a position for a thermocouple was fabricated. This reactor configuration allowed parallel reactions, with the temperature of the aluminum insert governing the temperature in each reactor vessel. Reactions performed in parallel under the conditions shown in Scheme 1 established good reproducibility within three reactors in a single experiment (yield=75±2%), and multiple experiments demonstrated good reproducibility between experiments (n=6, yield=75±2%). In contrast, parallel reactions performed in three vessels loosely placed in a single Parr autoclave (in the absence of the aluminum insert) had poor tube-to-tube reproducibility (yield=32±28%). The difference between experimental setups was attributed to temperature aberrations within the reactor that were removed with the aluminum block. A second key factor relates to effective mixing catalyst and carboxylate substrate. Optimal mixing of reactants involved grinding (2-3 g) in a mortar and pestle for at least 5 minutes and provided 20% higher yield of 2,5-FDCA after thermal treatment than material mixed with a spatula or in a small mortar and pestle (0.2 g material). Extended grinding gave equivalent yields to the optimal time noted above. Reactions that afforded appreciable 2,5-FDCA were visually identifiable by the change in color from the white of the staring material to red. Reaction mixtures heated at temperatures above 300° C. appeared darker in color, and this correlated with the formation of appreciable amounts of black intractable side-products. Analysis of the reaction mixture by X-ray photoelectron spectroscopy revealed only Cu(I), in mixtures of CuI and potassium furoate that have been heated at 300° C. under $CO_2$ for 1 hour as well as in the mixture of reactants that were kept at room temperature. In the absence of CuI, potassium furoate heated to 300° C. was recovered quantitatively, indicating that conversion required a catalyst such as CuI.

Scheme 1

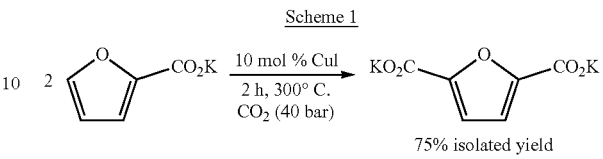

75% isolated yield

The isolated yield was 25% lower than the theoretical yield. The unaccounted-for-material could be side-products from the reaction including 2,4-FDCA and/or intractable solids or 2,5-FDCA lost during workup. Experiments were performed to identify the total yields of both 2,4- and 2,5-FDCA by analysis of the entire reaction mixture. The crude red solid obtained from the reactor vessel was partially soluble in DMSO or water. The insoluble material contained species derived from the copper catalyst and pyrolyzed organics, which accounted for a portion of the lower-than-theoretical yield. $^1$H NMR spectra in DMSO-$d_6$ of the soluble portion contained broad signals and could not be used to accurately quantify the products present. Instead, acidification of the aqueous solution precipitated pure 2,5-FDCA (75% isolated yield) (Scheme 2). Analysis of the remaining soluble portion by $^1$H NMR spectroscopy revealed 2,4-FDCA (7% yield), 2,5-FDCA (10% yield) and trace furoic acid (<1%) (Scheme 2).

Scheme 2

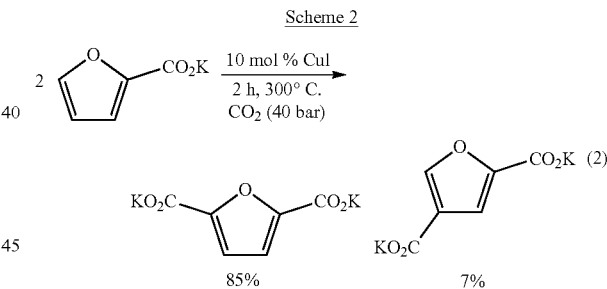

85%       7%

The product yields were sensitive to the reaction temperature. The isolated yield of 2,5-FDCA increased from 0 to 75% as the reaction temperature increases from 260-300° C. (Table 2). The maximum isolated yield of 2,5-FDCA was obtained in reactions heated at 300° C. Increased amounts of insoluble black materials form, and the isolated yields of 2,5-FDCA decreased in reactions performed at temperatures above 300° C.

TABLE 2

Temperature Effects on CuI-Catalyzed Furoate Disproportionation, Assessed by % Yield of Isolated 2,5-FDCA

| Temp (° C.)$^a$ | Isolated Yield of 2,5-FDCA (%)$^b$ |
|---|---|
| 260 | 0 |
| 280 | 20 (±2) |
| 290 | 70 (±2) |

TABLE 2-continued

Temperature Effects on CuI-Catalyzed Furoate Disproportionation, Assessed by % Yield of Isolated 2,5-FDCA

| Temp (° C.)[a] | Isolated Yield of 2,5-FDCA (%)[b] |
|---|---|
| 300 | 75 (±1) |
| 310 | 67 (±1) |

[a]Reaction conditions: 1.75 mmol potassium furoate, 0.18 mmol CuI, 2 hours under $CO_2$ (40 bar).
[b]Average of 3 experiments.

Carbon dioxide appears to have a number of roles in the reaction. First, it is needed for conversion to occur. Reaction mixtures after thermal treatment of potassium furoate under high pressure of $N_2$ (60 bar) but in the absence of $CO_2$ contained only starting materials, even in the presence of the CuI catalyst. As noted above, potassium furoate was also recovered quantitatively in experiments that lacked copper iodide. Thus, it was concluded that $CO_2$ and CuI interacted to generate an active catalytic species. Diffuse reflectance infrared spectra of solid mixtures of CuI potassium furoate, heated from room temperature to 400° C. under 15 bar of $CO_2$, unfortunately did not reveal new signals that might be assigned to copper carboxylate species. In addition, the apparent oxidation state of the catalyst was copper(I) before and after the catalytic conversion at 300° C. under carbon dioxide, as determined by X-ray photoelectron spectroscopy (XPS). Despite the lack of detectable effects of carbon dioxide on the copper catalyst, conversion increased as carbon dioxide pressure increased. For example, approximately 50% of potassium furoate was converted in experiments under only 1 bar of $CO_2$, whereas 73% conversion was observed under 10 bar of $CO_2$ with otherwise equivalent conditions. Second, the $CO_2$ pressure affected the yield by favoring the dicarboxylate product. 2,5-FDCA yields were lower in experiments with lower $CO_2$ pressure and higher with increased pressure (Table 3). For example, the only isolable species after thermolysis under 1 bar of $CO_2$ was the starting material, and 2,5-FDCA was not formed in detectable quantities even though half of the potassium furoate reacted. Increased pressure of $CO_2$ to 10 bar increased the 2,5-FDCA yield to 33%. More intractable black materials were formed in these low $CO_2$ pressure experiments than those at 40 bar of $CO_2$, suggesting that the amount of carbon dioxide affected the accessible reaction pathways. Moreover, higher carbon dioxide pressure also inhibited decomposition of the 2,5-FDCA product. Thermolysis of dipotassium 2,5-furandicarboxylate under only 1 bar of $CO_2$ (in the presence of CuI) resulted in a 20% loss of starting material after 1 hour, whereas the 2,5-FDCA yields at 40 bar were identical after 1 hour and 18 hours (Table 4). Decomposition likely occurred from both the carboxylate and the dicarboxylate under low pressure of $CO_2$. Because both starting material and products contained carboxylate moieties and similar trends were observed in potassium benzoate disproportionation reactions, it was inferred that the decomposition pathway to intractable black materials involves loss of the carboxylate.

TABLE 3

Pressure Effects on CuI-Catalyzed Furoate Disproportionation, Assessed by 2,5-FDCA Yield

| | Yield of 2,5-FDCA (%)[c] |
|---|---|
| $CO_2$ Pressure (bar)[a] | |
| 1 | 0 (0)[d] |
| 10 | 33 (0)[e] |
| 40 | 85 (75) |
| $N_2$ pressure (bar) | |
| 60[b] | 0 (0) |

[a]Conditions: 1.75 mmol potassium furoate, 0.18 mmol CuI, $CO_2$ atmosphere, 300° C., 1 hour;
[b]Nitrogen atmosphere;
[c]Isolated yield given within parenthesis;
[d]47% starting material;
[e]27% starting material.

TABLE 4

CuI-Catalyzed Conversion of Potassium Furoate and Yield of Dicarboxylic Acid Product[a]

| Time (h)[b] | Conversion (%)[c] | Diacid yield (%)[d] | Total yield of 2,5-FDCA (%)[e] | Selectivity: % 2,5-FDCA[f] | Isolated 2,5-FDCA[g] |
|---|---|---|---|---|---|
| 0.08 | 95 (±2) | 74 (±4) | 65 (±3) | 87 | 44 (±1) |
| 0.5 | >99 | 87 (±4) | 81 (±3) | 93 | 71 (±2) |
| 1 | >99 | 92 | 85 | 92 | 76 (±2) |
| 18 | >99 | 92 | 85 | 92 | 75 (±1) |
| 1[h] | >99 | 85 | 78 | 92 | 61 (±1) |

[a]Conditions: 10 mol % CuI, 40 bar $CO_2$, 300° C.;
[b]Time at the maximum reactor temperature (300° C.), excluding ca. 50 min. needed to reach temperature (conversion is minimal below 280° C.);
[c]% Conversion, defined as (moles potassium furoate$_{initial}$ − moles potassium furoate$_{time}$)/ moles potassium furoate$_{initial}$;
[d]Combined % yield of 2,4-FDCA and 2,5-FDCA;
[e]% Combined yield of 2,5-FDCA;
[f]Selectivity is defined as % yield of 2,5-FDCA/% yield of combined FDCA × 100;
[g]% Yield of pure 2,5-FDCA precipitated upon acidification of crude reaction mixture;
[h]320° C.

The rates of consumption of potassium furoate and formation of 2,5-FDCA were not equivalent, suggesting that the transformation proceeded through a multistep pathway involving a less reactive intermediate. First, disappearance of potassium furoate occurred rapidly at 300° C. Approximately 95% of starting material was consumed after 5 minutes, and the starting material was not detected in reaction mixtures heated for 30 minutes (>99%, Table 4). Although conversion of potassium furoate was high after 5 minutes, the crude 2,5-FDCA yield was only 65% of the theoretical yield at that time. Yields increased to 81% after 30 minutes and 85% after 1 hour, at which point the reaction was complete. Reaction mixtures allowed to heat for 18 hours at 300° C. provided equivalent yields to 1 hour-long experiment.

As noted above, the isomer 2,4-FDCA was a side product in the disproportionation of potassium furoate, and the reaction's selectivity for 2,5-FDCA vs the minor isomer was assessed to decouple the analysis of dicarboxylate forming pathways from those of decomposition. Interestingly, the selectivity for 2,5-FDCA (Table 4, column 5), calculated with respect to all quantified furanic species (2,5-FDCA+2,4-FDCA), was high (92%) at 300° C., as well as at higher temperatures (320° C.) and shorter reaction times (30 min) when the yield of dicarboxylate was not maximized. These data suggested that the rates of CuI-catalyzed formation and decomposition of 2,4-FDCA and 2,5-FDCA were similar. In addition, this selectivity for 2,5-FDCA was significantly higher (92%) than the previous CdI$_2$ based catalyst (70%) (Thiyagarajan et al., "Concurrent Formation of Furan-2,5- and Furan-2,4-dicarboxylic Acid: Unexpected Aspects of the Henkel Reaction," RSCAdv. 3:15678-86 (2013), which is hereby incorporated by reference in its entirety).

The catalyst loading of CuI had a significant effect on the ratio of 2,5-FDCA and 2,4-FDCA products. With 1 mol % CuI, 99% of the FDCA formed was the 2,5 isomer, and only trace quantities of 2,4-FDCA were detected by $^1$H NMR spectroscopy. In contrast, 25 mol % CuI resulted in only 71% selectivity for 2,5-FDCA. 2,4-FDCA became the major product in reactions with 1 equivalent of CuI (59% selectivity for 2,4-FDCA). In addition, the higher ratios of 2,4-FDCA:2,5-FDCA increased the solubility of the 2,5-isomer in water, impeding the isolation and quantification of products from reactions with higher catalyst loading. For example, the isolated yield of 2,5-FDCA from the reaction with 25 mol % CuI was only 66%, partly as a result of poorer selectivity noted above. Although the 1 mol % CuI experiments gave higher selectivity, the conversion and 2,5-FDCA yields were only 65 and 7%, respectively, and longer reaction times (18 hours) did not improve the yield.

Most reported Henkel-type reactions rely on potassium as the cation in the carboxylate salt starting material (e.g., potassium benzoate or potassium furoate). Interestingly, the sodium salt of furoic acid was converted to 2,5-FDCA in 15% yield in a ZnCl$_2$-catalyzed disproportionation after 3 hours at 250° C. (compared to 52 from potassium furoate) (Pan et al., "Catalytic Conversion of Furfural into a 2,5-Furandicarboxylic Acid-Based Polyester with Total Carbon Utilization," Chem Sus Chem 6:47-50 (2013), which is hereby incorporated by reference in its entirety). CuI is a more effective catalyst for conversion of sodium furoate compared to the reported zinc system; however, the CuI catalyst requires temperatures above 300° C. Sodium furoate heated at 300° C. for 2 hours, under conditions that are otherwise identical to optimal conditions for conversion of potassium furoate, returned only starting material. At 320° C., the 2,5-FDCA yield increased to 10% and to 59% at 340° C. (Table 5) (Scheme 3). As discussed above, reactions of potassium furoate with CuI were optimal at temperatures from 280 to 300° C. Thus, the higher temperature required for sodium furoate was counterbalanced by the increased lifetime of sodium salts of both starting material and products. Clearly, the counter cation was involved in both the disproportionation reaction and the decomposition pathway.

TABLE 5

Temperature Effects on CuI-Catalyzed Sodium Furoate Disproportionation$^a$

| Temperature (° C.) | Isolated Yield of 2,5-FDCA (%) |
|---|---|
| 300 | 0 |
| 320 | 10 |
| 340 | 59 |

$^a$Conditions: 10 mol % CuI, CO$_2$ (40 bar), 2 hours.

Copper iodide was also a catalyst for the disproportionation of potassium benzoate to terephthalate (Scheme 4). As noted above, benzoate-based Henkel reactions typically occur at higher temperatures than those required for potassium furoate disproportionation, and the CuI-based system follows this trend. Heating potassium benzoate and 10 mol % CuI to 350° C. under 40 bar of CO$_2$ provided terephthalic acid in 60% yield after 16 hours and workup (Scheme 4). Sodium benzoate, heated under these conditions, was recovered quantitatively.

Scheme 4

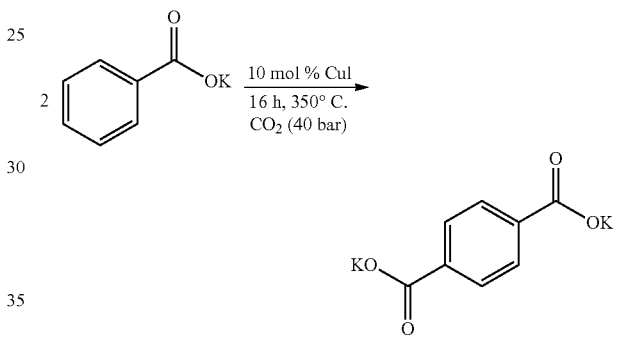

The Henkel isomerization of dipotassium isophthalate into terephthalate was also catalyzed by CdI$_2$ in a process related to the Henkel disproportionation. Under similar conditions to those used for potassium benzoate disproportionation (Scheme 4), terephthalic acid was formed in 21.4% yield from a CuI-catalyzed isophthalate isomerization (Table 6) (Scheme 5). 25.2% of the isophthalate was converted to a black intractable solid. While such material was present in all the processes described here, it was most significant for this isophthalate isomerization. Reactions of disodium isophthalate at 350° C. provided only isophthalic acid after workup. Sodium benzoate and disodium isophthalate have been reported to be converted to terephthalate in the presence of CdI$_2$, although they required temperatures of 450° C. (Ratusky, "Transcarboxylation Reactions of Salts of Organic Acids. XIX. The Effect of Various Cations on the Course of Transcarboxylation and the Catalytic Effect of Some of These Cations," Collect. Czech. Chem. Commun. 38:74-86 (1973), which is hereby incorporated by reference in its entirety).

Scheme 3

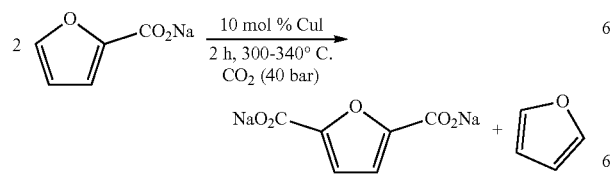

Scheme 5

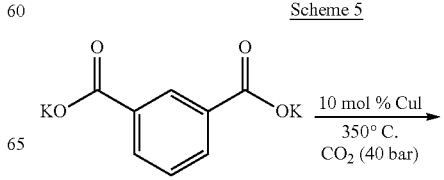

-continued

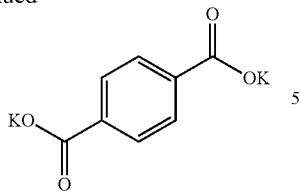

TABLE 6

CuI-Catalyzed Isomerization of Dipotassium
Isophthalate to Terephthalate[a]

| Time (h)[b] | Isophthalic Acid (%)[c] | Terephthalic Acid (%)[d] |
|---|---|---|
| 1 | 84.5 | 0 |
| 3 | 54.2 | 14.5 |
| 16 | 53.4 | 21.4 |

[a]Conditions: 10 mol % CuI, $CO_2$ (40 bar), 350° C., run in triplicate;
[b]Less than 100% of the phthalate isomers are present in the crude product, attributed to decomposition;
[c]% recovery of isophthalic acid (moles of isophthalic acid recovered/moles isophthalate starting materials × 100%);
[d]% yield of terephthalic acid.

In conclusion, it was demonstrated that CuI, an inexpensive, commercially available material, is an effective catalyst for the disproportionation or isomerization of aromatic carboxylates to dicarboxylates. As in the conventional group 12 catalysts for the Henkel reaction, the copper (I) center is initially a closed shell $d^{10}$ configuration, and the oxidation state of the catalyst appears to be unchanged at the completion of the reaction. The open-shell copper(II) was reported to be ineffective as a catalyst for Henkel-type reactions. Thermolysis of potassium furoate using well-defined copper (II) precursors, such as copper sulfate, provided only trace amounts of 2,5-FDCA. Cadmium(II), zinc(II), and now copper(I) catalysts performed best with iodide as the counter anion, but other iodide salts (such as potassium iodide) were not effective. Compared to the previous state-of-the-art Henkel catalyst $CdI_2$, total yield of 2,5-FDCA has increased to 85% versus from 64% with $CdI_2$.

The drawbacks for CuI as a catalyst is the increased reaction temperature to 300° C. from 260° C. and the need for high pressures of $CO_2$. Carbon dioxide appears to be involved in the catalytic pathway and also inhibited decomposition of the potassium carboxylates. Despite these points, the copper iodide-catalyzed process is much faster at 300° C. compared to group 12 iodides at 260° C. Moreover, the selectivity for 2,5-FDCA compared to isomeric 2,4-FDCA or decomposition products was improved at lower ratios of CuI to potassium furoate. It is likely that a reactor configuration that facilitates in situ solid phase mixing in combination with thermal and pressurized conditions described in the present application could lead to additional improvements in yield and selectivity with lower amounts of catalyst. The conversion of sodium carboxylates and benzoate salts may also provide advantages in the application of this system.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A process for preparation of a compound of Formula (I):

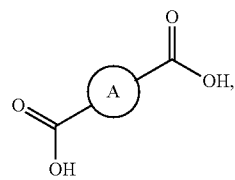

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;

or a salt thereof, comprising:
providing a compound of Formula (II):

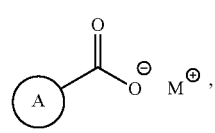

wherein M is a metal;
providing an oxide of carbon;
providing a copper(I) containing compound; and
reacting the compound of Formula (II) with the oxide of carbon in the presence of the copper(I) containing compound to form the compound of Formula (I).

2. A process for preparation of a compound of Formula (I):

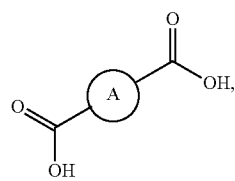

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;

or a salt thereof, comprising:
providing a compound of Formula (III):

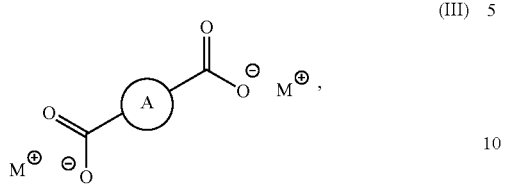

(III)

wherein M is a metal;
providing a copper(I) containing compound; and
reacting the compound of Formula (III) in the presence of the copper(I) containing compound to form the compound of Formula (I).

3. The process according to claim 1 further comprising:
providing an alkylating agent;
reacting the compound of Formula (I) with the alkylating agent to form the compound of Formula (IV):

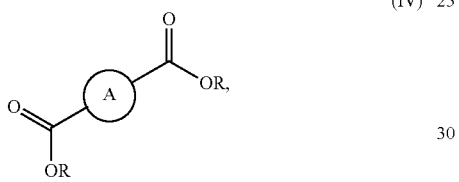

(IV)

wherein R is $C_{1-6}$ alkyl.

4. The process according to claim 3, wherein the alkylating agent is R—W and wherein W is OH, halogen, $-OSO_2CF_3$, $OSO_2C_6H_4Me$, or an alkene in the presence of p-toluenesulfonic acid.

5. The process according to claim 1, wherein said reacting leads to formation of a reaction mixture, said process further comprising:
dissolving the reaction mixture in the hot water.

6. The process according to claim 5 further comprising:
filtering the dissolved reaction mixture.

7. The process according to claim 6 further comprising:
acidifying the filtered reaction mixture using a mineral acid.

8. A process for preparation of a compound of Formula (IV):

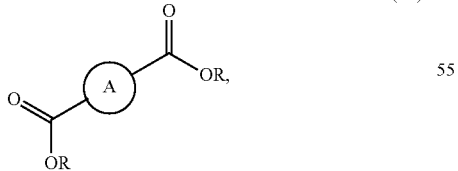

(IV)

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;
R is $C_{1-6}$ alkyl;
or a salt thereof, comprising:
providing a compound of Formula (I):

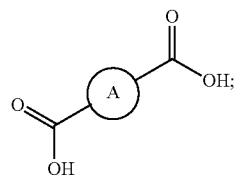

(I)

providing an alkylating agent;
reacting the compound of Formula (I) with the alkylating agent to form the compound of Formula (IV).

9. The process according to claim 8, wherein said providing a compound of Formula (I) comprises:
providing a compound of Formula (II):

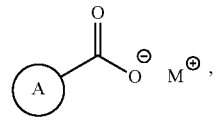

(II)

wherein M is a metal;
providing an oxide of carbon;
providing a copper(I) containing compound; and
reacting the compound of Formula (II) with the oxide of carbon in the presence of the copper(I) containing compound to form the compound of Formula (I).

10. A process for preparation of a compound of Formula (IV):

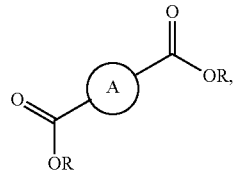

(IV)

wherein

is aryl or heteroaryl, wherein aryl and heteroaryl can be optionally substituted from 1 to 3 times with a substituent selected independently at each occurrence thereof from $C_{1-6}$ alkyl, $C_{3-8}$ cycloalkyl, aryl, and heteroaryl;
R is $C_{1-6}$ alkyl;

or a salt thereof, comprising:
providing a compound of Formula (II):

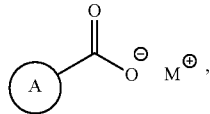
(II)

wherein M is a metal;
providing a oxide of carbon;
providing a copper(I) containing compound;
providing an alkylating agent; and
reacting the compound of Formula (II) with the oxide of carbon in the presence of the copper(I) containing compound and the alkylating agent to form the compound of Formula (IV).

11. The process according to claim 1, wherein

is selected from the group consisting of binaphtyl, biphenyl, phenyl, and furyl, wherein the binaphtyl, biphenyl, phenyl, and furyl can be optionally substituted from 1 to 3 times with a substituent selected independently at each occurrence thereof from $C_{1-6}$ alkyl, $C_{3-8}$ cycloalkyl, aryl, and heteroaryl.

12. The process according to claim 1, wherein

is selected from the group consisting of fused aryl and fused heteroaryl, wherein the fused aryl and fused heteroaryl can be optionally substituted from 1 to 3 times with a substituent selected independently at each occurrence thereof from $C_{1-6}$ alkyl, $C_{3-8}$ cycloalkyl, aryl, and heteroaryl.

13. The process according to claim 8, wherein the alkylating agent is R—W, wherein W is OH, halogen, —OSO$_2$CF$_3$, OSO$_2$C$_6$H$_4$Me, or an alkene in the presence of p-toluenesulfonic acid.

14. The process according to claim 1, wherein the oxide of carbon is carbon dioxide.

15. The process according to claim 1, wherein the copper (I) containing compound is a copper(I) halide.

16. The process according to claim 15, wherein the copper(I) containing compound is CuI.

17. The process according to claim 1, wherein M is an alkali metal.

18. The process according to claim 17, wherein M is K or Na.

19. The process according to claim 1, wherein the copper (I) containing compound is present in an amount of from 0.001 to 25 mol %.

20. The process according to claim 19, wherein the copper(I) containing compound is present in an amount of from 5 to 15 mol %.

21. The process according to claim 1, wherein said reacting is carried out at a pressure ranging from 1 to 60 bar.

22. The process according to claim 21, wherein said reacting is carried out at a pressure ranging from 30 to 50 bar.

23. The process according to claim 1, wherein said reacting is carried out at a temperature above 250° C. and below the decomposition temperature of the compound of Formula (II).

24. The process according to claim 23, wherein said reacting is carried out at a temperature above 280° C. and below 400° C.

25. The process according to claim 23, wherein said reacting is carried out at a temperature above 290° C. and below 360° C.

26. The process according to claim 1, wherein said reacting is carried out for a period of time ranging from 0.0005 to 24 hours.

27. The process according to claim 26, wherein said reacting is carried out for a period of time ranging from 0.05 to 18 hours.

28. The process according to claim 1, further comprising:
mixing the compound of Formula (II) with the copper(I) containing compound prior to said reacting to form a reaction mixture.

29. The process according to claim 28, wherein said mixing is conducted for at least 5 minutes.

* * * * *